United States Patent [19]
Wilk

[11] Patent Number: 5,280,782
[45] Date of Patent: Jan. 25, 1994

[54] VARIABLE LENGTH LAPAROSCOPIC RETRACTOR AND ASSOCIATED METHOD OF USE

[76] Inventor: Peter J. Wilk, 185 W. End Ave., New York, N.Y. 10023

[21] Appl. No.: 892,036

[22] Filed: Jun. 2, 1992

Related U.S. Application Data

[63] Continuation-in-part of Ser. No. 833,510, Feb. 11, 1992, which is a continuation-in-part of Ser. No. 792,379, Nov. 15, 1991, Pat. No. 5,152,279.

[51] Int. Cl.⁵ .................... A61B 17/02; A61B 1/32
[52] U.S. Cl. ................................ 128/20; 128/17; 606/198
[58] Field of Search ............... 128/17, 20, 3, 18, 19; 606/191, 198, 106, 197; 604/104–109

[56] References Cited

U.S. PATENT DOCUMENTS

| | | |
|---|---|---|
| 817,973 | 4/1906 | Hausmann . |
| 2,474,857 | 7/1949 | Newman ............................ 128/20 |
| 3,517,128 | 6/1970 | Hines . |
| 3,525,329 | 8/1970 | Zeimer ............................... 604/104 |
| 3,570,475 | 3/1971 | Weinstein ........................... 128/20 |
| 3,744,481 | 7/1973 | McDonald . |
| 3,769,980 | 11/1973 | Karman ............................ 128/17 |
| 3,810,462 | 5/1974 | Szpur . |
| 4,116,232 | 9/1978 | Rabban ............................ 128/20 |
| 4,350,151 | 9/1982 | Scott . |
| 4,702,230 | 10/1987 | Pelta . |
| 4,726,356 | 2/1988 | Santilli et al. . |
| 4,817,587 | 4/1989 | Janese ............................. 128/20 |
| 4,966,130 | 10/1990 | Montaldi . |
| 5,052,373 | 10/1991 | Michelson . |
| 5,113,846 | 5/1992 | Hiltebrandt et al. ............. 604/105 |

*Primary Examiner*—Richard J. Apley
*Assistant Examiner*—Donna L. Maraglio
*Attorney, Agent, or Firm*—R. Neil Sudol; Henry D. Coleman

[57] ABSTRACT

A laparoscopic retractor device comprising an elongate rigid frame member insertable through a laparoscopic trocar sleeve into a patient's body, a rigid retractor member pivotably attached to a distal end of the frame member, and one or more components on the retractor member for enabling modification of an effective length or width of the retractor member. A variable length retractor member may have modular extension elements or a telescoping insert.

9 Claims, 9 Drawing Sheets

VARIABLE LENGTH LAPAROSCOPIC RETRACTOR AND ASSOCIATED METHOD OF USE

CROSS-REFERENCE TO A RELATED APPLICATION

This application is a continuation-in-part of commonly owned application Ser. No. 833,510 filed Feb. 11, 1992 which in turn is a continuation-in-part of commonly owned application Ser. No. 792,379 filed Nov. 15, 1991, now U.S. Pat. No. 5,152,279.

BACKGROUND OF THE INVENTION

This invention relates to a surgical instrument. More particularly, this invention relates to a retractor for use in laparoscopic surgery. This invention also relates to an associated surgical method.

In laparoscopic surgery, one or more openings are made in a patient's abdominal wall, usually by piercing the wall with the aid of a trocar. A laparoscope is inserted through one of the openings to enable a surgeon to see organs and tissues which are located in the patient's abdominal cavity. Usually, operating instruments such as grasping forceps and cutting tools are inserted into the abdominal cavity through ancillary openings made in the abdominal wall.

Some internal organs or tissues are disposed under other organs when the patient is lying on his or her back (the normal posture during laparoscopic surgery). The overlying organs must be lifted or otherwise displaced prior to operating on the underlying organs. Generally, a grasping forceps is used to grip an overlying organ and pull it upwardly to provide access to the desired surgical site. This procedure is frequently cumbersome, if not ineffective, to adequately expose the underlying organs and tissues.

OBJECTS OF THE INVENTION

An object of the present invention is to provide an improved technique for temporarily displacing an internal body organ of a patient during laparoscopic surgery.

Another object of the present invention is to provide an associated surgical instrument for use in laparoscopic surgery.

Another, more particular, object of the present invention is to provide a laparoscopic surgical retractor.

A further particular object of the present invention is to provide such a retractor which is easy to use and inexpensive to fabricate.

Yet another object of the present invention is to provide a laparoscopic retractor with a retractor member having an adjustable length.

An additional object of the present invention is to provide a a laparoscopic retractor with a retractor member having an adjustable width.

Other objects of the present invention will be apparent from the detailed descriptions and drawings included herein.

SUMMARY OF THE INVENTION

A laparoscopic retractor device comprises, in accordance with the present invention, an elongate rigid frame member insertable through a laparoscopic trocar sleeve into a patient's body, a rigid retractor member pivotably attached to a distal end of the frame member, and one or more components on the retractor member for enabling modification of an effective length of the retractor member.

Modifying the effective length of the retractor member facilitates use of the retractor instrument insofar as the instrument is readily adaptable to different surgical conditions.

Pursuant to one of several alternative specific embodiments of the present invention, the length modification component includes a connector at a free end of the retractor member for receiving an extension element to increase the effective length. The extension may itself be of different lengths. Particularly, the extension may comprise a plurality of modular units connectable to one another. Preferably, the units are firmly locked to one another to prevent inadvertant disassembly or partial disassembly of the retractor member while it is disposed in a patient's abdominal cavity.

Pursuant to another specific embodiment of the present invention, the length modification component includes at least one telescoping element slidably attached to the retractor member. The telescoping member may be disposed inside the main body of the retractor member.

Pursuant to a further specific embodiment of the present invention, the rectractor member is pivotably attached to a distal end of the frame member for swinging about a pivot axis fixed relative to the frame member, while the length modification component includes a connector part for varying the location of the retractor member with respect to the pivot axis. Thus, the retractor member is shortened by having a portion extending to the opposite side of the frame member in the manner of a T-configuration during use of the instrument.

Pursuant to yet another specific embodiment of the present invention, the retractor member is removably fastened to the frame member, thereby enabling substitution of another retractor member of a different effective length.

A method for use in laparoscopic surgery comprises, in accordance with the present invention, the steps of (a) providing a retractor instrument comprising an elongate frame member and a substantially rigid retractor member movably mounted to the frame member, (b) forming an opening in a patient's abdominal wall, (c) inserting the frame member and the retractor member through the opening, (d) maintaining the retractor member and the frame member in substantially parallel relation to one another during the step of inserting, and (e) upon a partial insertion of the retractor instrument into an abdominal cavity of the patient, manipulating the retractor instrument to shift the retractor member so that the retractor member is angled with respect to the frame member. Additional steps in the method include (f) estimating a desired effective length of the retractor member and (g) further manipulating the retractor instrument to modify the effective length of the retractor member. The frame member is manipulated so that the retractor member with the modified effective length engages a selected internal body organ of the patient. Upon engagement of the selected internal body organ with the retractor member, a force is exerted on the frame member, while the retractor member is maintained in an angled orientation with respect to the frame member, whereby the position of the selected internal body organ in the abdominal cavity of the patient is shifted.

According to another feature of the present invention, the steps of estimating and further manipulating are performed prior to the insertion of the frame member and the retractor member through the opening in the patient's abdominal wall.

Pursuant to a more specific feature of the present invention, manipulation of the retractor member comprises the step of attaching an extension element to a free end of the retractor member. Alternatively, manipulation of the retractor member comprises the step of sliding a telescoping element with respect to a body portion of the retractor member. As another alternative, manipulation of the retractor member comprises the step of removing the retractor member from the frame member and attaching thereto another retractor member having a different effective length. Where the retractor member is pivotably attached to a distal end of the frame member for swinging about a pivot axis fixed relative to the frame member, manipulation of the retractor member includes the step of varying the location of the retractor member with respect to the pivot axis.

A laparoscopic retractor device comprises, in accordance with the present invention, an elongate rigid frame member insertable through a laparoscopic trocar sleeve into a patient's body, a rigid retractor member pivotably attached to a distal end of the frame member and a component on the retractor member for enabling modification of an effective width thereof.

According to another feature of the present invention, the width modification component includes a web member attached to the retractor member and means for spreading the web member from a collapsed configuration to an extended configuration.

The means for spreading may include an elongate spreader bar fastened to the web member and pivotably connected to the retractor member at a free end thereof. The width modification component further includes a plurality of elongate reinforcement ribs attached to the web member.

The width modification component may alternatively take the form of at least one auxiliary retractor member pivotably mounted to the frame member.

The present invention provides an improved technique for temporarily displacing an internal body organ of a patient during laparoscopic surgery. A laparoscopic retractor in accordance with the present invention has a retractor member with a variable length and/or a variable width, thereby facilitating adaptation of the instrument to the particular conditions of a surgical procedure.

DETAILED DESCRIPTION

Figure 1:
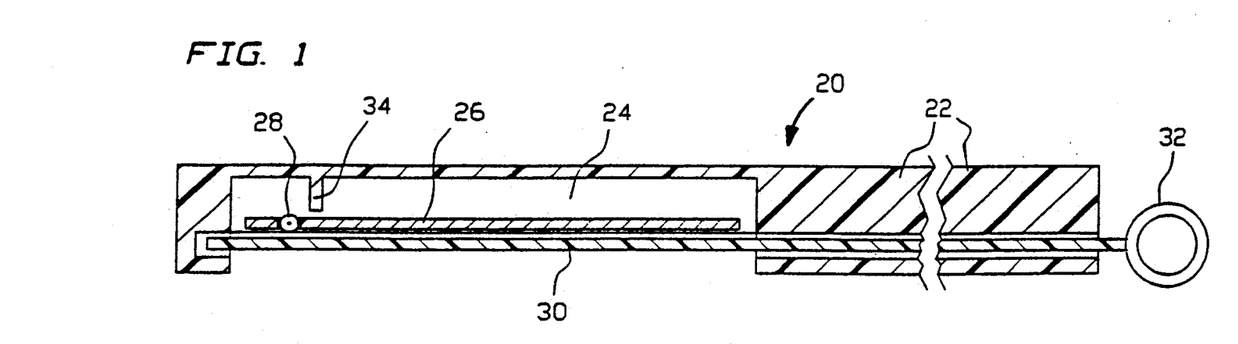
FIG. 1 is a schematic longitudinal cross-sectional view of a retractor for use in laparoscopic surgery, showing a retractor member in a closed or storage configuration.
Figure 2:
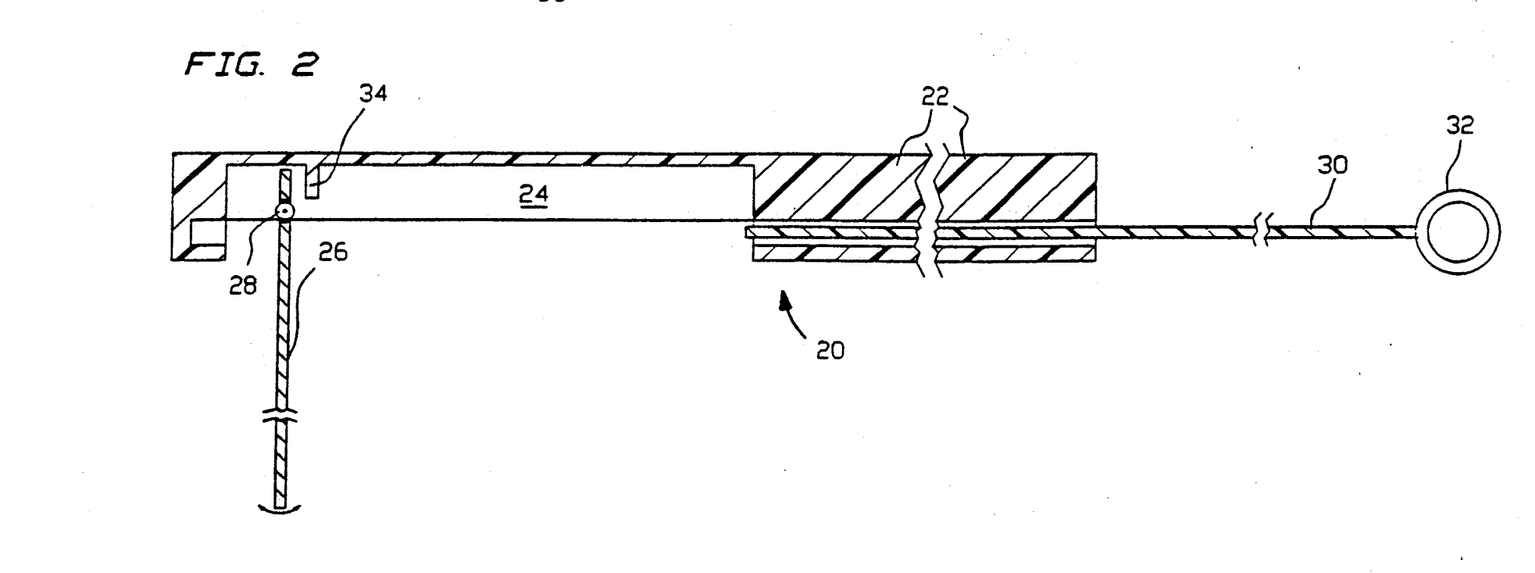
FIG. 2 is a schematic longitudinal cross-sectional view similar to FIG. 1, showing the retractor member of that drawing figure in an opened or use configuration.

As illustrated in FIGS. 1 and 2, a retractor 20 for use in laparoscopic surgery comprises a substantially rigid frame or body member 22 provided at a distal end with an elongate recess 24 for receiving a substantially rigid retractor arm 26 in a retracted, storage configuration. Retractor arm 26 is swingably mounted to frame or body member 22 at a pivot pin 28. During insertion of the laparoscopic retractor 20 through an opening formed in a patient's abdominal wall (more specifically, through a tubular member traversing the abdominal wall), retractor arm 26 is held in recess 24, in a substantially parallel orientation with respect to frame 22, by a slider element 30. Upon sufficient insertion of the distal end of retractor 20 into the abdominal cavity of the patient, slider 30 is grasped and pulled in a proximal direction via a finger ring 32 or other manual actuator part. The opening of recess 24 due to the sliding away of slider 30 frees retractor arm 26 to swing about pivot pin 28 under the force of gravity, whereby the retractor arm assumes an opened or use configuration shown in FIG. 2.

During a laparoscopic surgical procedure using laparoscopic retractor 20 of FIGS. 1 and 2, an opening is formed in a patient's abdominal wall, for example, through the use of a trocar. A tubular member is inserted through the opening in a conventional technique for maintaining the opening in a dilated state. Upon insertion of frame 22 and retractor arm 26 in the closed, mutually parallel configuration of FIG. 1 through the abdominal opening, slider 30 is shifted in the proximal direction to enable retractor arm 26 to rotate downwardly so that the retractor arm is angled essentially orthogonally with respect to frame 22, as shown in FIG. 2. Frame 22 is then manipulated so that retractor arm 26 engages a selected internal body organ of the patient, such as the liver. Upon engaging the selected internal body organ with retractor arm 26, the operating surgeon or attendant pulls on frame 22 to displace or shift the liver into an at least partially retracted position. During this retraction of the selected internal body organ, retractor arm 26 is maintained in an essentially orthogonal orientation with respect to frame 22 by virtue of an arrest or stop 34 on frame 22, which prevents or blocks further rotation of retractor arm 26.

Upon the completion of a laparoscopic surgical operation on an organ or tissues underlying the retracted organ, frame 22 is moved to disengage retractor arm 26 and the retracted internal body organ of the patient. Upon completing the disengagement of the retractor arm 26 and the internal body organ, the surgeon or attendant rotates retractor instrument 20 so that retractor arm 26 pivots in a reverse direction about pivot pin 28 and again assumes the substantially parallel configuration of FIG. 1. Slider 30 is then shifted in the distal direction to lock retractor arm 26 in recess 24. Frame 22 and retractor arm 26 are then withdrawn from the patient through the abdominal opening.

It is to be noted that it is not necessary for slider 30 to completely close recess 24 in order to lock retractor arm 26 in the closed or parallel configuration of FIG. 1. In fact, slider 30 need only overlap the proximal tip of retractor arm 26. It is to be further noted that retractor arm 26 may be maintained in parallel with respect to frame 22 solely by gravity. In that case, slider 30 may be omitted. During an insertion step of a laparoscopic procedure utilizing such a modified retractor instrument, the frame or body member is held to keep the retractor arm on the upper side. Upon sufficient insertion of the retractor instrument into the patient's abdominal cavity, the frame is rotated to allow the retractor arm to pivot downwardly under the force of gravity.

Figures 3, 6:
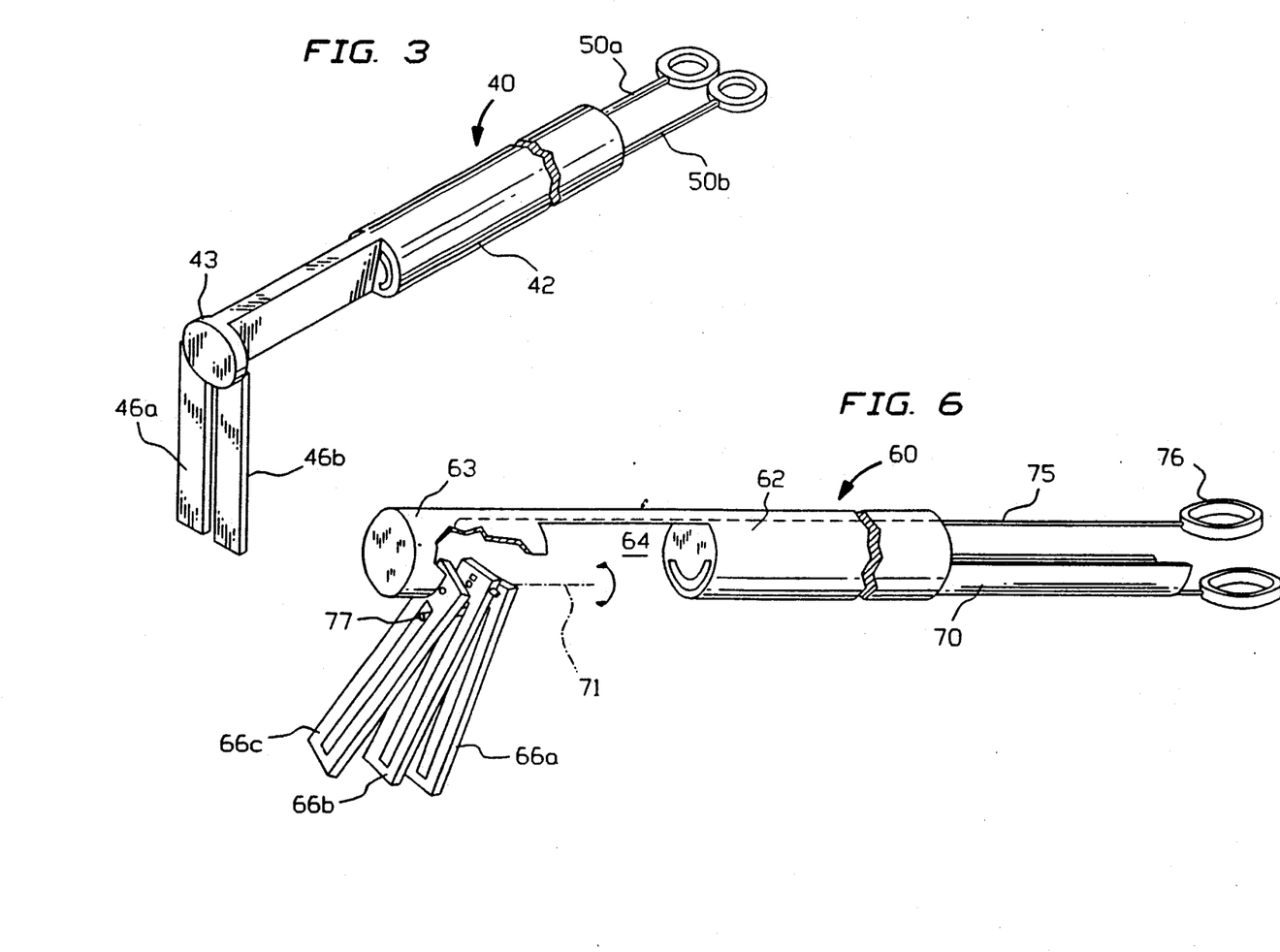
FIG. 3 is a schematic perspective view of another laparoscopic retractor, showing a pair of retractor members in an opened or use configuration.
FIG. 6 is a schematic side perspective view of yet another laparoscopic retractor.
Figures 4, 5:
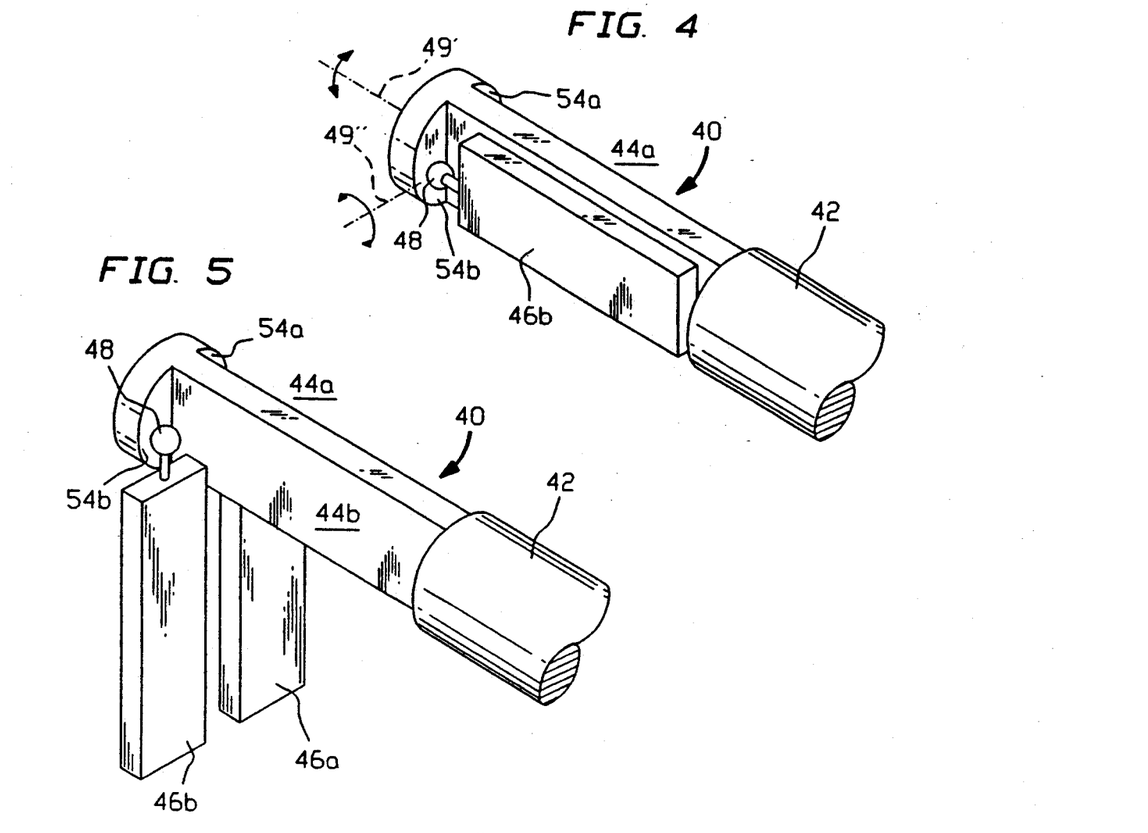
FIG. 4 is a partial perspective view, from a different angle, of the laparoscopic retractor of FIG. 3, showing the retractor members in a closed or storage configuration.
FIG. 5 is a partial perspective view similar to FIG. 4, showing the retractor members in the opened configuration of FIG. 3.

As illustrated in FIGS. 3-5, another retractor instrument 40 comprises an elongate, essentially tubular, frame or body member 42 to a distal end 43 of which a pair of substantially rigid planar retractor arms 46a and 46b are pivotably secured. As shown in FIG. 4, retractor arms 46a and 46b are held parallel planes in respective recesses or chambers 44a and 44b by respective locking elements 50a and 50b (FIG. 3) which are slidably mounted to frame 42. Retractor arms 46a and 46b are pivotably attached to the distal end 43 of frame 42 via respective universal couplings 48 (only one shown in the drawings). Universal couplings 48 permit retractor arms 46a and 46b to pivot about two axes 49' and 49" (FIG. 4) upon a proximally directed stroke of locking elements 50a and 50b. Such a stroke of locking elements 50a and 50b opens recesses 44a and 44b and enables retractor arms 46a and 46b to fall under the force of gravity into the essentially orthogonal orientation of FIGS. 3 and 5 wherein arms 46a and 46b are in essentially the same plane. During use of retractor instrument 40 to retract an organ such as the liver, retractor arms 46a and 46b are maintained in their common plane essentially perpendicular to frame 42 by arresting surfaces 54a and 54b at the distal end 43 of frame 42.

It is to be noted that retractor instrument 20 of FIGS. 1 and 2 may be modified to assume specific design features of the embodiment of FIGS. 3-5. For example, retractor arm 26 may be pivotably connected to frame 22 via a universal type coupling. In addition, slider 30 may have an arcuate cross-section like locking elements 50a and 50b, rather than a rectangular cross section.

Similarly, retractor instrument 40 of FIGS. 3-5 may be altered to take on specific design elements shown in the embodiment of FIGS. 1 and 2. For example, retractor instrument 40 might have one integral locking element instead of two separate ones.

Figure 7A:
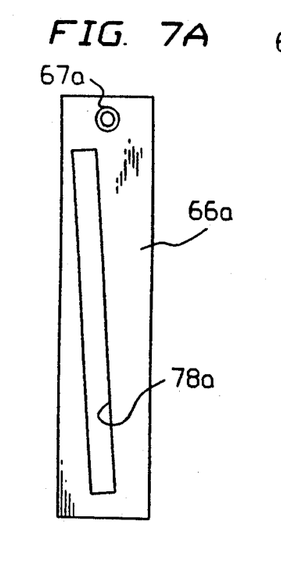
FIGS. 7A-7C are elevational views of three cooperating retractor members shown in FIG. 6.
Figure 7B:
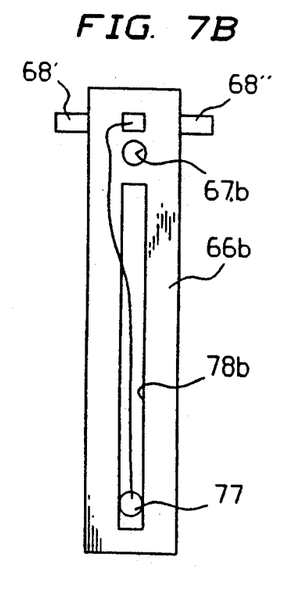
Figure 7C:
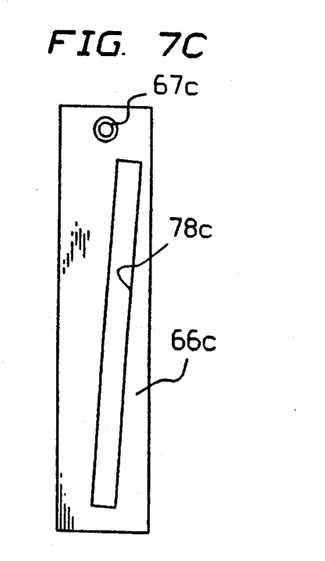

FIG. 6 and 7A-7C illustrate a further retractor instrument 60. Retractor instrument 60 is provided with three overlapping or interleaved retractor arms 66a, 66b, and 66c. Retractor arms 66a, 66b, and 66c are pivotably mounted to a distal end 63 of a frame or body member 62 via one or two pivot pins 68' and 68" on center retractor arm 66b. Retractor arms 66a, 66b, and 66c are held or locked in a recess or chamber 64 in frame 62 by a cross-sectionally arcuate slider element 70. Outer retractor arms 66a and 66c are pivotably mounted for rotating outwardly in opposite directions in the manner of a fan so that all three retractor arms 66a, 66b, 66c assume a triangular use configuration, as depicted in FIG. 6. Retractor arms 66a and 66c are pivotably connected to retractor arm 66b via mating lugs 67a and 67c which traverse a bore 67b in retractor arm 66b (FIGS. 7A-7C).

It is to be noted that retractor arms or plates 66a and 66c may be pivotably connected to center retractor arm 66b at a point above pivot pins 68' and 68", rather than below the pivot pins, as illustrated in FIGS. 6 and 7A-7C. Alternatively, retractor arms 66a and 66c may be pivotably connected directly to frame 62 via respective universal type couplings (not shown).

To implement the swinging of retractor arms 66a and 66c about an axis 71 extending substantially parallel to frame 62, a wire 75 extends from a finger ring 76 at a proximal end of frame 62 to a pin or peg 77 which traverses camming slots 78a, 78b, and 78c in retractor arms 66a, 66b, and 66c, respectively. Slot 78b extends centrally with respect to center retractor arm 66b, while slots 78a and 78c are inclined with respect to outer retractor arms 66a and 66c. Cable is initially shifted in the distal direction so that peg 77 is located near the free ends of retractor arms 66a, 66b, and 66c while the arms are disposed in a stacked parallel configuration inside recess 64. After slider 70 has been shifted in the proximal direction and after retractor arms 66a, 66b, and 66c have fallen into an orthogonal orientation, wire 75 is pulled in the proximal direction to spread arms 66a, 66b, and 66c. After a laparoscopic surgical operation utilizing retractor instrument 60, is completed, frame 62 is shaken or vibrated to allow peg 77 to fall to the bottoms of slots 78a, 78b, and 78c. Frame 62 is then rotated to swing retractor arms 66a, 66b, and 66c back into the storage position inside recess 64. Slider 70 is then shifted in the distal direction to lock the retractor arms in the closed, storage position and the retractor instrument is withdrawn from the abdominal cavity of the patient.

Figure 8:
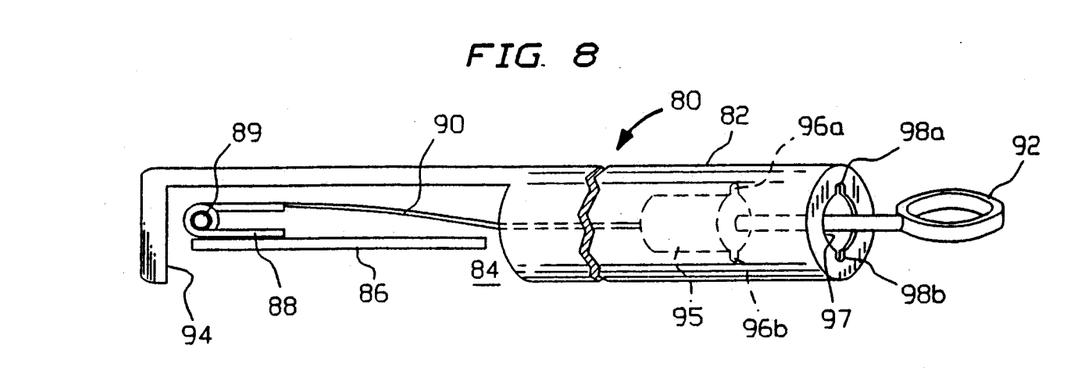
FIG. 8 is partially a perspective view and partially a side elevational view of a further laparoscopic retractor, showing a retractor member in a closed or storage configuration.
Figure 9:
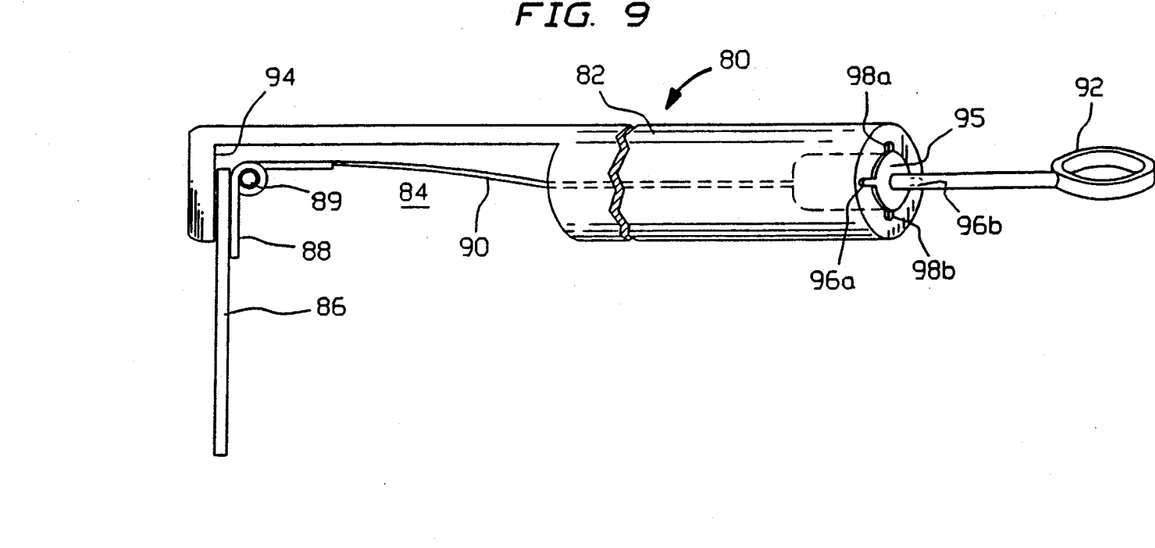
FIG. 9 is a view similar to FIG. 8, showing the retractor member of that figure in an opened or use orientation.

As shown in FIG. 8 and 9, an additional retractor instrument 80 comprises a frame or body member 82 defining a recess 84 in which a retractor arm 86 is disposed during a storage or insertion phase of a laparoscopic procedure. A leaf spring 88 is prestressed or biased to maintain retractor arm 86 in recess 84 in a parallel orientation with respect to body member 82, as illustrated in FIG. 8. Leaf spring 88 extends around a lug or rod element 89 and is connected to a cable 90. Upon a pulling of cable 90 via a finger ring 92 attached thereto, leaf spring 88 partially straightens out owing to its being forced along rod element 89, and thereby rotates retractor arm 86 into an essentially orthogonal orientation shown in FIG. 9. The further unbending of leaf spring 88 and the further concomitant rotation of retractor arm 86 is stopped by an arresting surface 94 at the distal end of body member 82. A locking element in the form of a plug 95 bearing at one end two opposing fingers 96a and 96b is connected to cable 90 for locking the cable during a retraction operation. During a withdrawing stoke of cable 90, plug 95 with fingers 96a and 96b passes through an aperture 97 with finger-like extensions 98a and 98b at a proximal end of body member 82. Upon the passage of fingers 96a and 96b outside of body member 82, plug 95 is twisted to angularly displace fingers 96a and 96b with respect to extensions 98a and 98b, thereby locking cable 90 in a fixed position in opposition to the restoring force provided by the spring bias of leaf spring 88. The above-described process is reversed to close retractor instrument 80.

Figure 10:
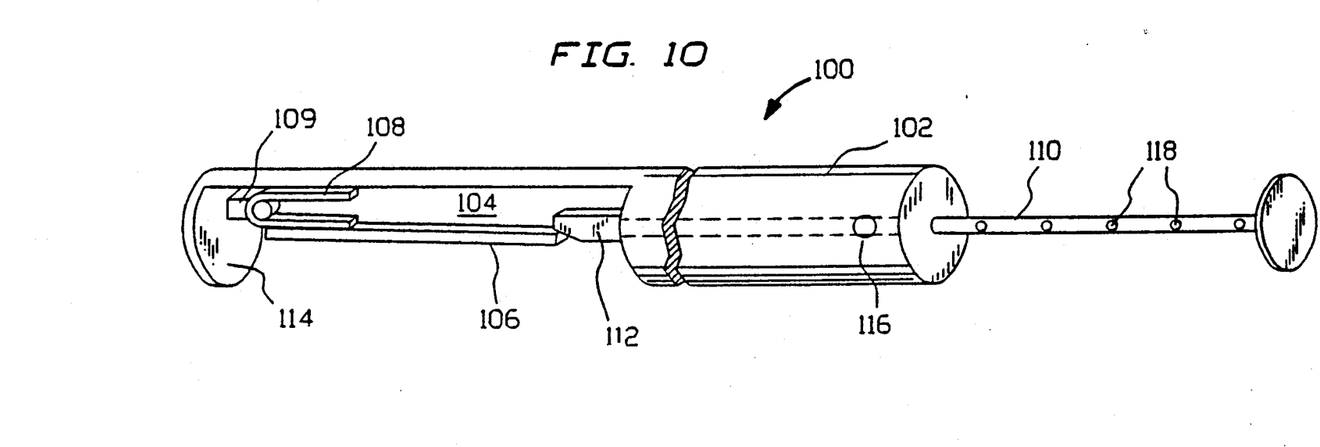
FIG. 10 is a perspective view of yet another laparoscopic retractor, showing a retractor member in a closed or storage orientation with respect to a frame member.
Figure 11:
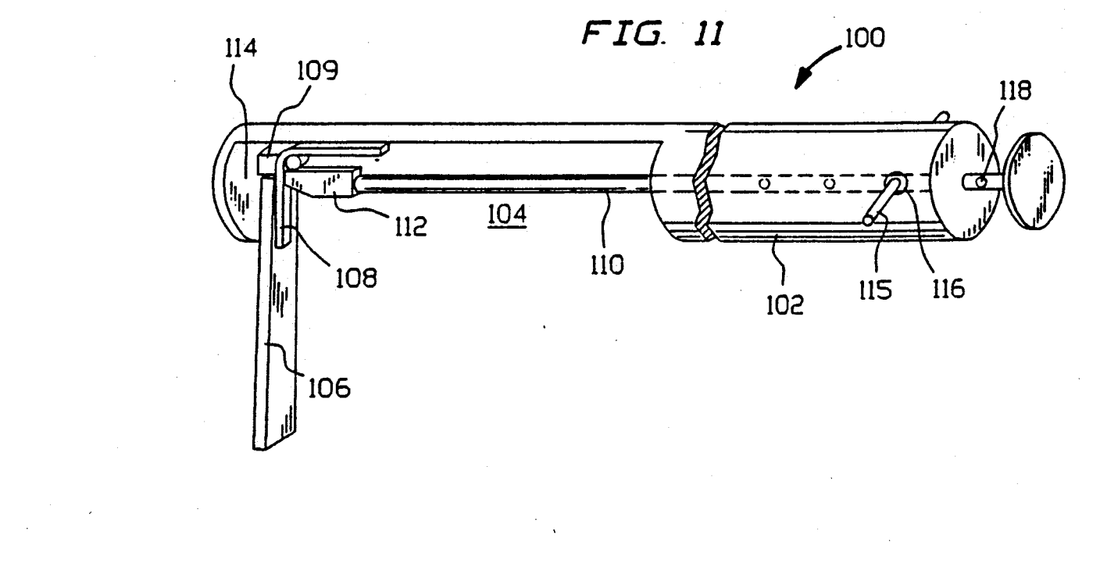
FIG. 11 is a view similar to FIG. 10, showing the retractor member of that figure in an opened orientation extending orthogonally with respect to the frame member.

FIGS. 10 and 11 illustrate yet another retractor instrument 100 which comprises a frame or body member 102 defining a recess 104 in which a retractor arm 106 is disposed during a storage or insertion phase of a laparoscopic procedure. A leaf spring 108 is prestressed or biased to maintain retractor arm 106 in recess 104 in a parallel orientation with respect to body member 102, as illustrated in FIG. 10. Leaf spring 108 is fixed to frame member 102 at 109. A push rod 110 provided at a distal end with a wedge 112 is slidably mounted to frame 102. During a retractor opening step, leaf spring 108 is partially straightened out by wedge 112 in response to a distally directed stroke of push rod 110. Retractor arm 106 is thereby rotated into an essentially orthogonal orientation shown in FIG. 11. Further unbending of leaf spring 108 and further concomitant rotation of retractor arm 106 is stopped by an arresting surface 114 at the distal end of body member 102. A locking element in the form of a pin 115 is inserted through openings 116 (only one visible in the drawing) in frame 102 and through an aligned opening in an array of openings 118 in push rod 110, to maintain retractor arm 106 in the opened configuration shown in FIG. 11.

As illustrated in FIGS. 12A-12D, a laparoscopic retractor comprises a tubular outer member 120 in which an elongate rod or frame member 122 is slidably inserted. Rod 122 is provided at a proximal end with a flange 124 for facilitating manual sliding of the rod relative to tubular member 120 and is further provided at a distal end with a substantially planar retractor member 126 pivotably attached to rod 122 at pivot point 128. Pivot point 128 is spaced from each end of retractor member 126.

Figure 12A:
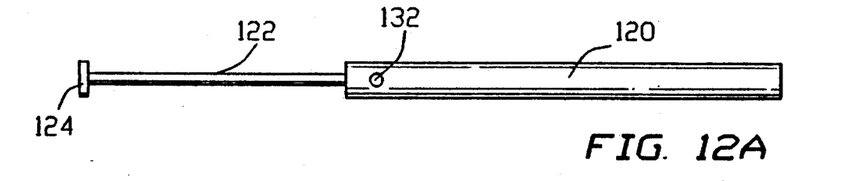
FIGS. 12A-12D are schematic side elevational views of a laparoscopic retractor, showing different steps in the utilization of the retractor.

During an initial step of a laparoscopic retracting procedure, illustrated in FIG. 12A, rod 122 is maintained in a proximal disposition relative to tubular member 120 so that retractor member 126 is at least partially withdrawn into tubular member 120. This relative configuration of components 120, 122 and 126 ensures that retractor member 126 is locked in a position extending essentially parallel to rod 122.

Figure 12B:
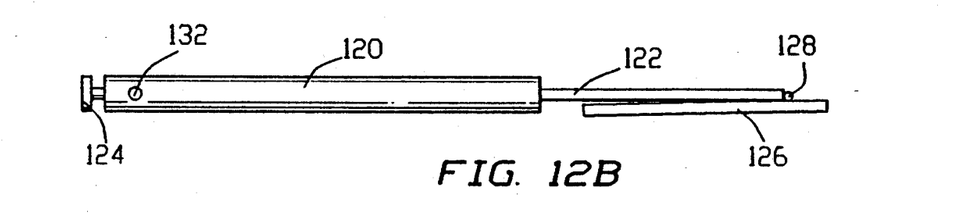
Figure 12C:
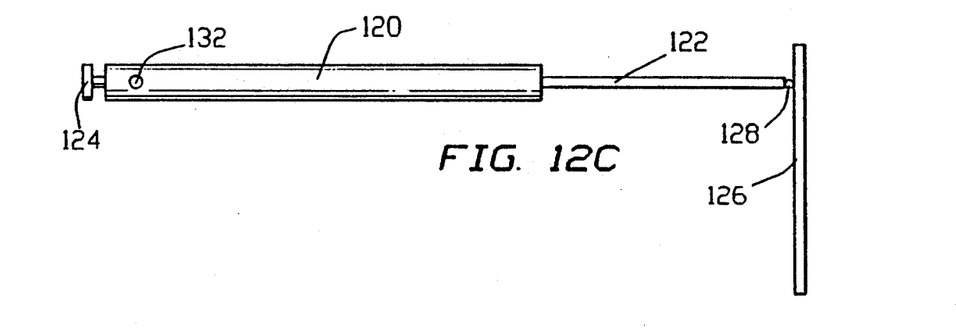

Upon an insertion of tubular member 120 through a patient's abdominal wall (not shown) so that a distal portion of the tubular member projects into the abdominal cavity, rod 122 is pushed in the distal direction so that retractor member 126 comes completely out of tubular member 120, as illustrated in FIG. 12B. At that point, retractor member 126 swings downwardly about pivot point 128 under the action of gravity, as depicted in FIG. 12C. It may be necessary to rotate rod 122 about its longitudinal axis (not designated) in order to enable the pivoting of retractor member 126.

Figure 12D:
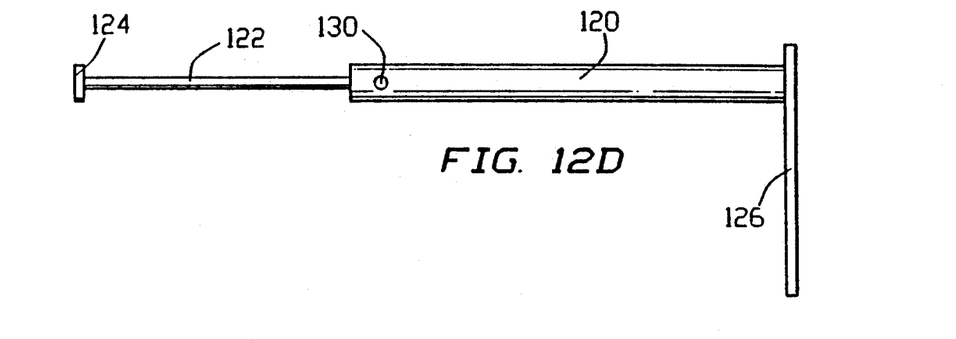

Upon the swinging of retractor member 126 into the lowered or extended position of FIG. 12C, rod 122 is pulled back in the proximal direction relative to tubular member 120, thereby bringing retractor member 126 into a locking engagement with a distal edge or end of tubular member 120, as shown in FIG. 12D. A pin 130 may be inserted through a hole 132 (FIGS. 12A-12C) in tubular member 120 to temporarily lock rod 122 to tubular member 120. It is to be noted that retractor member 126 and tubular member 120 or rod 122 together form a substantially L-shaped use configuration wherein retractor member 126 extends substantially perpendicularly with respect to tubular member 120 and rod 122. Upon an exerting of force on rod 122 and tubular outer member 120, retractor member 126 may be used to pull or push an internal body organ of a patient, to permit access to underlying organs or tissues.

Figure 13A:
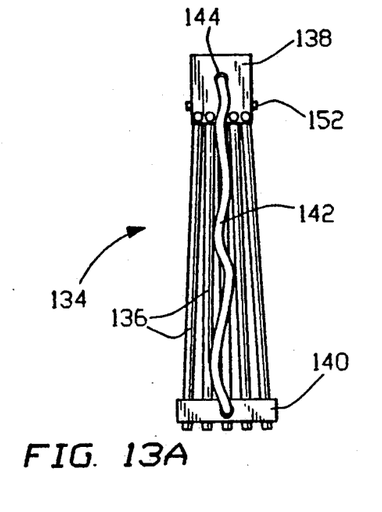
FIGS. 13A and 13B are schematic front elevational views of a spreadable retractor member, showing different steps in the utilization of the retractor member.
Figure 13B:
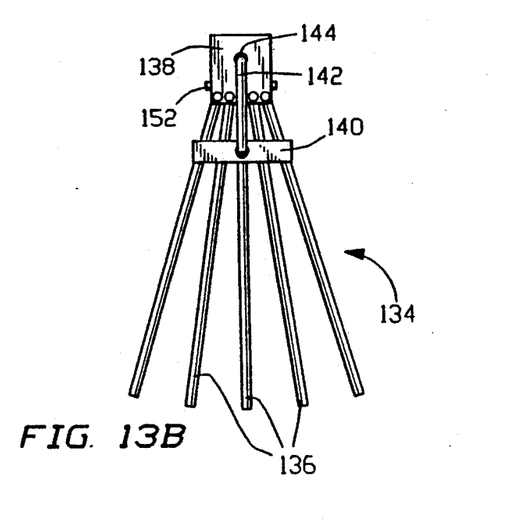

As illustrated in FIGS. 13A and 13B, a retractor member 134 of a laparoscopic type retractor shown in FIGS. 14A-14E comprises a plurality of rods 136 each pivotably attached at one end to a bracket or base 138. Rods 136 traverse respective bores (not shown) in a relatively massive slider member 140. A wire 142 traverses an opening 144 in bracket 138 and is connected at one end to slider member 140. Upon a placement of tension on wire 142, slider member 140 slides along rods 136 from free ends thereof towards bracket 138, thereby spreading rods 136 in the manner of a hand-held fan and adjusting retractor member 134 from a pre-use configuration shown in FIG. 13A to a spread use configuration shown in FIG. 13B.

As illustrated in FIGS. 14A-14E, a laparoscopic retractor incorporating retractor member 134 comprises a tubular outer member 146 in which an elongate frame member or shaft 148 is slidably inserted. Shaft 148 is provided at a proximal end with a flange 150 for facilitating manual sliding of the shaft relative to tubular member 146 and is further provided at a distal end with retractor member 134. Bracket 138 of retractor member 134 is pivotably attached to shaft 148 at pivot elements 152. Pivot elements 152 define a pivot axis (not shown) spaced from each end of retractor member 134.

Figure 14A:
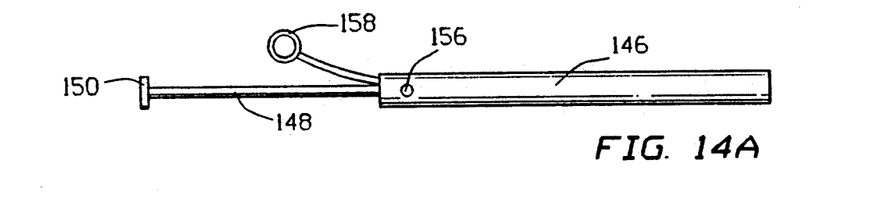
FIGS. 14A-14E are schematic side elevational views of a laparoscopic retractor incorporating the retractor member shown in FIGS. 13A and 13B, showing successive stages in the utilization of the retractor.

During an initial step of a laparoscopic retracting procedure, illustrated in FIG. 14A, shaft 148 is maintained in a proximal disposition relative to tubular member 146 so that retractor member 134 is at least partially withdrawn into tubular member 146. This relative configuration of components 146, 148, and 134 ensures that retractor member 134 is locked in a position extending essentially parallel to shaft 148 and tubular member 146.

Figure 14B:
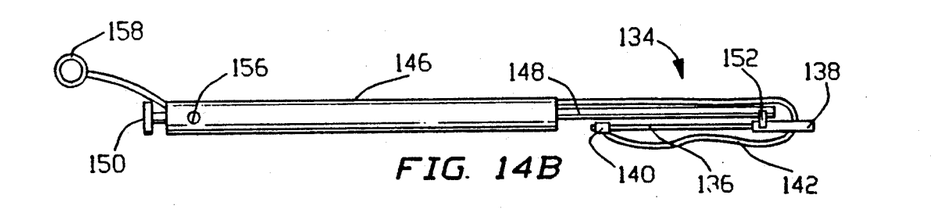
Figure 14C:
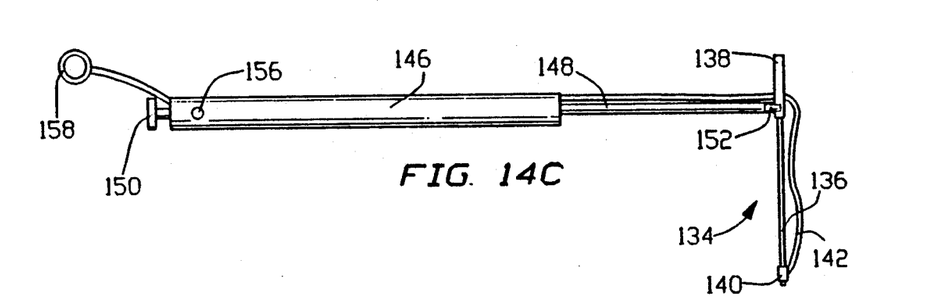

Upon an insertion of tubular member 146 through a patient's abdominal wall (not shown) so that a distal portion of the tubular member projects into the abdominal cavity, shaft 148 and tubular member 146 are shifted relative to one another so that retractor member 134 comes completely out of tubular member 146, as illustrated in FIG. 14B. At that point, retractor member 134 swings downwardly about pivot elements 152 under the action of gravity, as depicted in FIG. 14C. It may be necessary to rotate shaft 148 about its longitudinal axis (not shown) in order to enable the pivoting of retractor member 134.

Figure 14D:
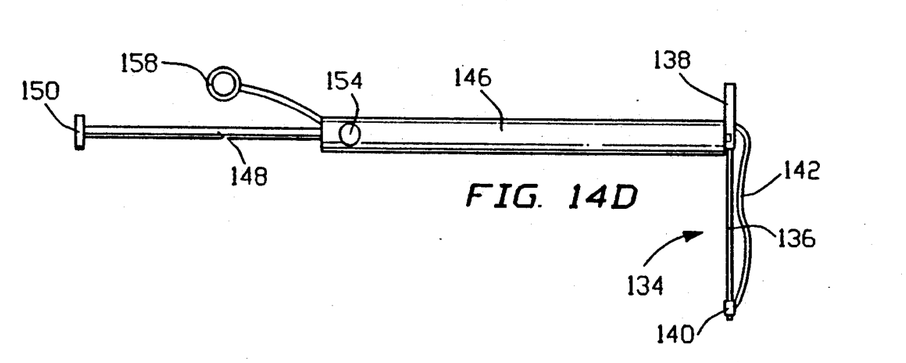
Figure 14E:
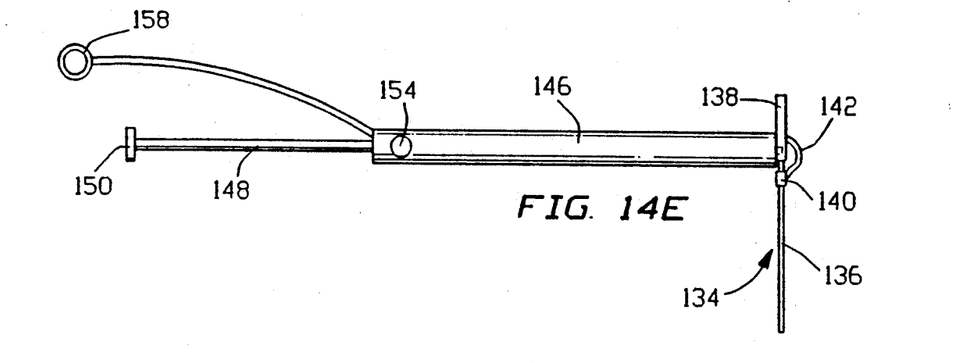

Upon the swinging of retractor member 134 into the lowered or extended position of FIG. 14C, shaft 148 and tubular member 146 are shifted relative to one another to bring bracket 138 into a locking engagement with a distal edge or end of tubular member 146, as shown in FIG. 14D. A pin 154 may be inserted through a hole 156 (FIGS. 14A-14C) in tubular member 146 to temporarily lock shaft 148 to tubular member 146. It is to be noted that retractor member 134 and tubular member 146 or shaft 148 together form a substantially L-shaped use configuration wherein rods 136 extend substantially perpendicularly with respect to tubular member 146 and shaft 148.

Wire 142 extends from slider member 140 through opening 144 and tubular outer member 146 to a ring 158 disposed at the proximal end of the tubular outer member. Upon the pulling of retractor member 134 in the proximal direction so that bracket 138 is locked against the distal end of tubular outer member 146, as illustrated in FIG. 14D, a surgeon or other operator pulls on wire 142 via ring 158, thereby shifting slider member 140 upwardly along rods 136 towards bracket 138, to spread rods 136 into the configuration of FIG. 13B. Retractor member 134 may now be used to pull or push a relatively large internal body organ of a patient, to permit access to underlying organs or tissues.

To withdraw the retractor of FIGS. 14A-14E upon the termination of a retraction procedure, the tension on wire 142 is relaxed (a lock may be provided to maintain that tension during the operation), whereupon slider member falls to the lower ends of rods 136, drawing the rods together into the configuration of FIG. 13A. Shaft 148 may then be turned about its longitudinal axis to cause rods 136 and slider member 140 to collapse back upon shaft 148. Shaft 148 is then pulled in the proximal direction relative to tubular member 146, thereby withdrawing retractor member 134 into tubular member 146.

Figure 15A:
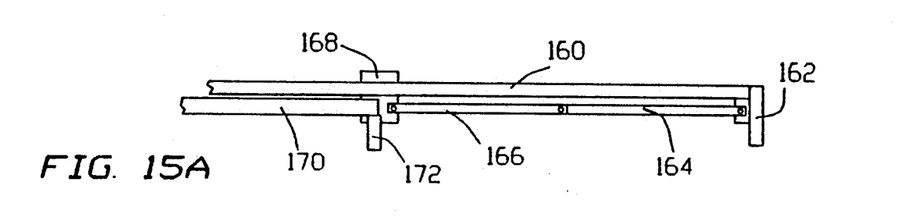
FIGS. 15A and 15B are schematic side elevational views of another laparoscopic retractor, showing a pre-use or insertion configuration and a use or extended configuration.
Figure 15B:
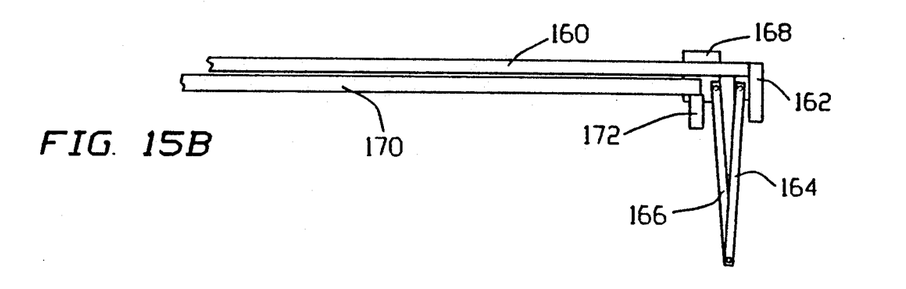

As depicted in FIGS. 15A and 15B, another retractor for use particularly in laparoscopic surgery comprises an elongate body member 160 having a flange 162 at a distal end. A first retractor member 164 is pivotably attached at a distal end to body member 160 and is pivotably attached at a proximal end to a second retractor member 166. A proximal end of retractor member 166 is pivotably connected to a slider member 168 which is slidably fastened to body member 160. Slider member 168 is connected to the distal end of a push-pull rod 170 and carries a flange or stop 172. Upon a pushing of rod 170 in the distal direction, retractor members 164 and 166 fold outwardly, as shown in FIG. 15B. Flanges or stops 162 and 172 limit swinging of retractor members 164 and 166 during a retraction operation. Flanges or stops 162 and 172 may be omitted, insofar as the different points of connection of retractor members 164 and 166 to body member 160 limit the rotation the two members can undergo.

Figure 16:
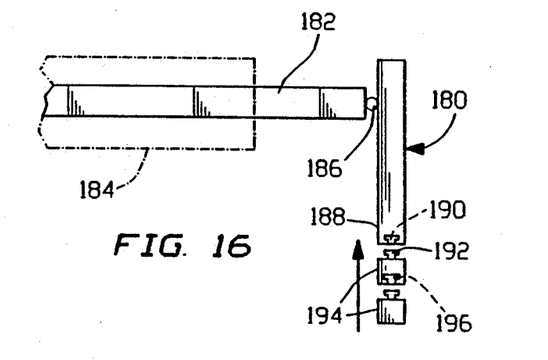
FIG. 16 is a schematic partial side elevational view of a laparoscopic retractor instrument with a variable length retractor member, in accordance with the present invention.

As illustrated in FIG. 16, a laparoscopic retractor instrument with a variable length retractor member 180 comprises a frame member 182 insertable with a tubular outer member 184 through a laparoscopic trocar sleeve into a patient's body. Retractor member 180 is pivotably attached via a hinge element 186 to a distal end of frame member 182. A free end 188 of retractor member 180 is provided with a recess 190 for receiving in a snap-lock fit a resilient projection 192 on a modular extension element 194. Each such modular extension element 194, for example, in a kit, is provided with both projection 192 and a matching snap-lock recess 196 for receiving the projection of another modular extension element 194, thereby enabling a piecewise or incremental increase in the length of retractor member 180, depending on the requirements of the particular surgical procedure.

Figure 17:
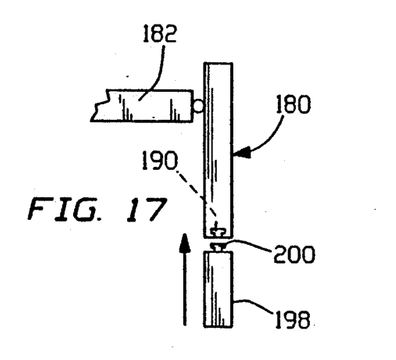
FIG. 17 is a schematic partial side elevational view of a laparoscopic retractor instrument with a variable length retractor member, similar to that illustrated in FIG. 16.

Alternatively, as illustrated in FIG. 17, a longer extension element 198 may be used instead of two or more modular elements 194. Extension element 198 is likewise provided at one end with a snap-lock projection 200 insertable into recess 190 for locking the extension element to free end 188 of retractor member 180 prior to the insertion of the retractor instrument through a trocar sleeve or cannula during a laparoscopic procedure.

It is to be noted that extension elements 194 are firmly locked to one another to prevent inadvertant disassembly or partial disassembly of retractor member 180 while it is disposed in a patient's abdominal cavity.

It is to be further noted that extension elements may be attached to the free end of a retractor member by any of a number of equivalent connector mechanisms. Such equivalent mechanisms include, but are not limited to, pressure-sensitive adhesives, pins or detents, screws, and dovetailing components.

Figure 18:
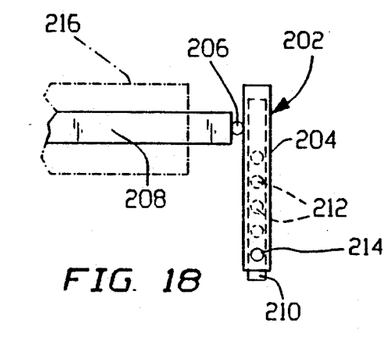
FIG. 18 is a schematic partial side elevational view of another laparoscopic retractor instrument with a variable length retractor member, in accordance with the present invention.

As depicted in FIG. 18, another variable length retractor instrument comprises a retractor member 202 having an at least partially hollow rigid body portion 204 pivotably connected via a hinge 206 to a distal end of a rigid frame member 208. Slidably inserted inside body portion 204 is a length modifying component in the form of a telescoping element 210. Telescoping element 210 is provided with a plurality of apertures or recesses 212 spaced from one another along the length of the telescoping element for receiving a locking pin (not illustrated) inserted through an opening 214 in body portion 204.

In using the retractor assembly of FIG. 18, an estimate of the required length of retractor member 202 is made prior to insertion of the instrument into a patient via a laparoscopic trocar sleeve. Telescoping element 210 is pulled out of body portion 204 by an amount sufficient to provide the required effective length of retractor member 202, a pin being inserted through opening 214 and an aperture 212 aligned therewith to thereby lock telescoping element 210 to the body portion 204. As described hereinabove with reference to FIGS. 12A-12D, retractor member 202 is pivoted so that it is parallel with frame member 208. Frame member 208 and retractor member 202 are then inserted into an outer tube 216 and the entire assembly is inserted through a trocar sleeve or cannula so that a distal end of the laparoscopic retractor assembly is located within a patient's abdominal cavity. The remainder of the procedure is similar to that described hereinabove with reference to FIGS. 12A-12D. If an adjustment in retractor member length is required, the retractor assembly may be temporarily removed from the patient.

Figure 19:
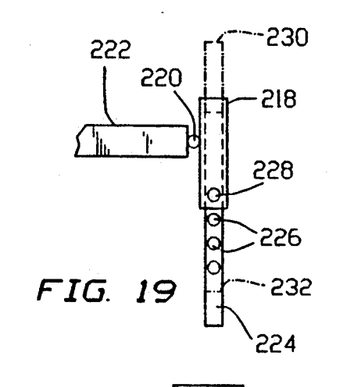
FIG. 19 is a schematic partial side elevational view of yet another laparoscopic retractor instrument with a variable length retractor member, in accordance with the present invention.

As shown in FIG. 19, another retractor instrument comprises a sleeve 218 pivotably connected via a hinge 220 to a distal end of a rigid frame member 222. Slidably inserted inside sleeve 218 is a retractor member 224. Retractor member 224 is provided with a plurality of apertures or recesses 226 spaced from one another along the length of the retractor member for receiving a locking pin (not illustrated) inserted through an opening 228 in sleeve 218. As illustrated by dot dash lines 230, retractor member 224 may be displaced relative to a pivot axis defined by hinge 220, thereby modifying the effective length of retractor member 224, as indicated at 232. Thus, retractor member 224 is effectively shortened by having a portion 230 extending to the opposite side of frame member 222 in the manner of a T-configuration during use of the instrument.

It is to be understood that the locking pin (not shown) insertable through apertures 212 and 226 of the retractor members 202 and 224 of FIGS. 18 and 19 is made of a resilient material or is otherwise constructed to prevent accidental dislodgement of the pin from the respective aperture or recess 212 or 226 during use of the laparoscopic retractor assembly. It is to be additionally understood that the locking pin (not shown) and cooperating apertures 212 and 226 of the retractor members 202 and 224 of FIGS. 18 and 19 may be replaced by other suitable locking mechanisms such as adhesive strips, nuts and bolts, snap-lock elements, detents, latches and force-lock fitted wedges. Other equivalent locking mechanisms are available to those skilled in the art.

Figure 20:
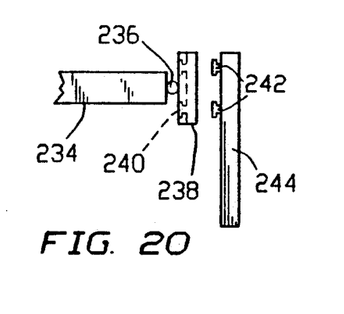
FIG. 20 is a schematic partial side elevational view of an additional laparoscopic retractor instrument with a variable length retractor member, in accordance with the present invention.

As illustrated in FIG. 20, yet another retractor instrument includes a frame member 234 with a hinge element 236 pivotably securing a bracket or channel element 238 to the distal end of the frame member. Bracket 238 is provided with a plurality of apertures 240 for receiving snap-lock projections 242 on a retractor member 244, thereby locking retractor member 244 to frame member 234 prior to use of the retractor instrument during a laparoscopic procedure. A plurality of retractor members 244 of different lengths may be provided in a kit (not shown) with frame member 234. Prior to use of the retractor instrument, the retractor member 244 of the desired length is selected to correspond with estimated length requirements.

Alternatively, retractor member 244 may be provided with a plurality of additional snap-lock projections (not shown) enabling an adjustment of the position of the retractor member relative to bracket 238 and hinge element 236, thereby modifying the effective length of retractor member 244. Thus, retractor member 244 is effectively shortened by having a portion (not illustrated) extending to the opposite side of frame member 234 in the manner of a T-configuration during use of the instrument.

Of course, different types of connectors may be provided on bracket 238 and retractor member 244 for coupling the bracket and the retractor member to one another prior to use of the laparoscopic instrument.

The retractor instruments of FIGS. 16, 17, 19 and 20 are used in a manner similar to that described above with reference to FIG. 18 and FIGS. 12A-12D. The lengths of the respective retractor members may be adjusted subsequently to the commencement of the surgical procedures upon a temporary withdrawal of the retractor instruments from the patient. In that event, the snap-lock elements in the retractor instruments of FIGS. 16, 17 and 20 form sufficiently fast connections to prevent the retractor members from disassembling inadvertently inside the patient but are releasable from each other to enable adjustment.

Figure 21:
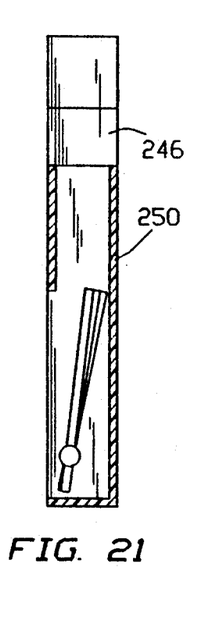
FIG. 21 is a schematic partial rear elevational view of a laparoscopic retractor instrument with a variable width retractor member, in accordance with the present invention, showing a width extension element in a collapsed configuration.
Figure 22:
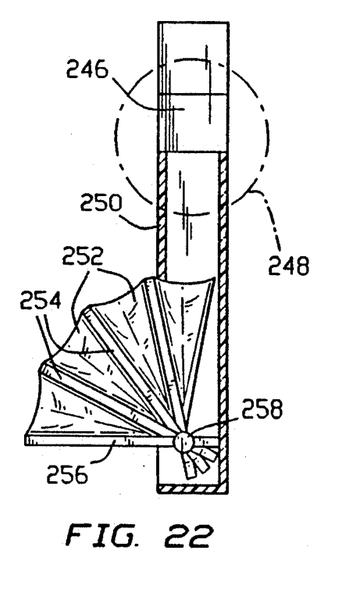
FIG. 22 is a view similar to FIG. 21, showing the width extension element in an extended configuration.

As depicted in FIGS. 21 and 22, a variable width laparoscopic retractor device comprises an elongate rigid frame member 246 insertable with a tubular outer member 248 through a laparoscopic trocar sleeve (not shown) into a patient's body. A rigid retractor member 250 pivotably attached to a distal end of frame member 246 is provided at a free end with a spreadable web 252 (FIG. 22) which is reinforced with a plurality of radially extending ribs 254 and provided along a free edge with a relatively massive spreader bar 256.

During an insertion step of a laparoscopic procedure utilizing the retractor instrument of FIGS. 21 and 22, web 252 is disposed in a collapsed configuration inside retractor member 250, as illustrated in FIG. 21. Upon an insertion of the distal end of frame member 246 into a patient's abdominal cavity, the frame is turned about its longitudinal axis to allow retractor member 250 to pivot into a use configuration angled with respect to frame member 246. In addition, a turning of frame member 246 about its longitudinal axis (perpendicular to the plane of the drawing) enables gravity to pivot spreader bar 256 and reinforcement ribs 254 about a pin 258 fixed to retractor member 250. The pivoting of spreader bar 256 serves to unfold web 252 from its collapsed configuration (FIG. 21) to an extended use configuration (FIG. 22). Reinforcement ribs 245 and spreader bar 265 are the active components in increasing the width of retractor member 250, i.e., ribs 354 and bar 256 transmit force required to move an organ inside a patient. Web 252 serves at least in part to space ribs 254 from one another and to move the ribs alternately in and out of retractor member 250.

It is to be noted that retractor arms 66a, 66b, and 66c (FIGS. 6 and 7A-7C) and rods 136 (FIGS. 13A and 13B) also serve to increase the effective width of the respective retractor members. In those cases, as well as in the embodiment of FIGS. 21 and 22, a plurality of relatively rigid elongate elements are pivotably connected to a retractor member for spreading apart from one another upon insertion into a patient.

Although the invention has been described in terms of particular embodiments and applications, one of ordinary skill in the art, in light of this teaching, can generate additional embodiments and modifications without departing from the spirit of or exceeding the scope of the claimed invention. For example, the length modification and width modification elements of a retractor member in accordance with the present invention may be combined to provide a single retractor assembly with both a variable effective length and a variable effective width.

In addition, with reference to FIGS. 21 and 22, retractor member 250 may be one component in a kit of similar retractor members (not shown) having spreadable width-extending webs and reinforcement ribs of different sizes and different locations on the respective retractor members. Moreover, some such retractor members may have fan-like extensions on two sides, not just the one side, as illustrated in FIGS. 21 and 22. The different retractor members may be alternately connected to frame member 246 to adapt the retractor instrument to different operating conditions.

Accordingly, it is to be understood that the drawings and descriptions herein are offered by way of example to facilitate comprehension of the invention and should not be construed to limit the scope thereof.

What is claimed is:

1. A laparoscopic retractor device comprising:
   an elongate rigid frame member insertable through a laparoscopic trocar sleeve into a patient's body;
   a rigid retractor member pivotably attached to a distal end of said frame member, said retractor member having a free end;
   an extension element;
   connector means on said free end of said retractor member for enabling a mounting of said extension element to said free end and only to said retractor member so that an effective length of said retractor member is increased.

2. The device defined in claim 1 wherein said means for enabling includes means for removably fastening said retractor member to said frame member, thereby enabling substitution of a retractor member of a first effective length for another retractor member of a second effective length.

3. A laparoscopic retractor device comprising:
   an elongate rigid frame member insertable through a laparoscopic trocar sleeve into a patient's body;
   a rigid retractor member pivotably attached to a distal end of said frame for motion between an insertion configuration parallel to said frame member and a use configuration extending at an angle with respect to said frame member, said retractor member having an effective length and a free end; and
   means for removably fastening said retractor member to said frame member, thereby enabling substitution of another retractor member of a different effective length for said rigid retractor member.

4. The device defined in claim 3 wherein said means for removably fastening includes means for releasably locking said rigid retractor member to said frame member.

5. A method for use in laparoscopic surgery, comprising the steps of:
   (a) providing a retractor instrument comprising an elongate frame member and a substantially rigid retractor member movably mounted to said frame member, said retractor member having modification means for modifying the effective length of said retractor member;
   (b) forming an opening in a patient's abdominal wall;
   (c) inserting said frame member and said retractor member through said opening;
   (d) maintaining said retractor member and said frame member in substantially parallel relation to one another during said step of inserting;
   (e) upon a partial insertion of the retractor instrument into an abdominal cavity of the patient, manipulating the retractor instrument to shift said retractor member so that said retractor member is angled with respect to said frame member;
   (f) estimating a desired effective length of said retractor member;
   (g) further manipulating said retractor instrument via said modification means to modify the effective length of said retractor member, said steps of estimating and further manipulating being performed prior to the insertion of said frame member and said retractor member through said opening;
   (h) manipulating said frame member so that said retractor member with the modified effective length engages a selected internal body organ of the patient;
   (i) upon engaging the selected internal body organ with said retractor member, exerting a force on said frame member; and
   (j) maintaining said retractor member in an angled orientation with respect to said frame member during said step of exerting, whereby the position of the selected internal body organ in the abdominal cavity of the patient is shifted.

6. The method defined in claim 5 wherein said step of further manipulating said retractor member comprises the step of attaching an extension element to a free end of said retractor member.

7. The method defined in claim 5 wherein said step of further manipulating said retractor member comprises the step of removing said retractor member from said frame member and attaching thereto another retractor member having a different effective length.

8. The method defined in claim 5 wherein said retractor member is pivotably attached to a distal end of said frame member for swinging about a pivot axis fixed relative to said frame member, further comprising the step of varying the location of said retractor member with respect to said pivot axis.

9. A laparoscopic retractor device comprising:
   an elongate rigid frame member insertable through a laparoscopic trocar sleeve into a patient's body;
   a rigid retractor member pivotably attached to a distal end of said frame member, said retractor member having a free end, said retractor member also having a longitudinal axis and an effective length measured along said axis; and
   attachment means at a plurality of spaced points along said retractor member for releasably attaching said retractor member to said frame member at selectably different points along said retractor member, thereby enabling modification of said effective length of said retractor member.

* * * * *

UNITED STATES PATENT AND TRADEMARK OFFICE
CERTIFICATE OF CORRECTION

PATENT NO. : 5,280,782
DATED : January 25, 1994
INVENTOR(S) : Peter J. Wilk

It is certified that error appears in the above-indentified patent and that said Letters Patent is hereby corrected as shown below:

```
Column 13, line 43, insert --member-- after "frame".
```

Signed and Sealed this

Twenty-second Day of November, 1994

Attest:

BRUCE LEHMAN

*Attesting Officer*    *Commissioner of Patents and Trademarks*